United States Patent
Lidgard (10) Patent No.: US 9,710,596 B2
(45) Date of Patent: *Jul. 18, 2017

(54) METHODS FOR QUANTIFYING NUCLEIC ACID VARIATIONS

(71) Applicant: Exact Sciences Corporation, Madison, WI (US)

(72) Inventor: Graham Lidgard, Madison, WI (US)

(73) Assignee: EXACT SCIENCES CORPORATION, Madison, WI (US)

( * ) Notice: Subject to any disclaimer, the term of this patent is extended or adjusted under 35 U.S.C. 154(b) by 96 days.

This patent is subject to a terminal disclaimer.

(21) Appl. No.: 13/683,756

(22) Filed: Nov. 21, 2012

(65) Prior Publication Data

US 2014/0141417 A1 May 22, 2014

(51) Int. Cl.
| | |
|---|---|
| G06F 19/20 | (2011.01) |
| C12Q 1/68 | (2006.01) |
| G06F 19/18 | (2011.01) |
| G06F 19/24 | (2011.01) |

(52) U.S. Cl.
CPC ............ *G06F 19/20* (2013.01); *C12Q 1/686* (2013.01); *C12Q 1/6851* (2013.01); *C12Q 2537/143* (2013.01); *C12Q 2537/164* (2013.01); *C12Q 2561/109* (2013.01); *G06F 19/18* (2013.01); *G06F 19/24* (2013.01)

(58) Field of Classification Search
CPC ............ C12Q 1/6844–1/686; C12Q 2561/109
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,338,671 A | 8/1994 | Scalice et al. | |
| 5,494,810 A | 2/1996 | Barany et al. | |
| 5,639,611 A | 6/1997 | Wallace et al. | |
| 5,773,258 A | 6/1998 | Birch et al. | |
| 5,786,146 A | 7/1998 | Herman et al. | |
| 5,965,408 A | 10/1999 | Short | |
| 7,662,594 B2 | 2/2010 | Kong et al. | |
| 8,361,720 B2 | 1/2013 | Oldham-Haltom et al. | |
| 2006/0252032 A1* | 11/2006 | Aslanukov et al. | 435/5 |
| 2007/0202525 A1 | 8/2007 | Quake et al. | |
| 2009/0253142 A1 | 10/2009 | Allawi et al. | |
| 2012/0122088 A1 | 5/2012 | Zou et al. | |
| 2012/0122106 A1 | 5/2012 | Zou et al. | |

FOREIGN PATENT DOCUMENTS

WO    2005023091    3/2005

OTHER PUBLICATIONS

Allawi, H. T. et al. Invader plus method detects herpes simplex virus in cerebrospinal fluid and simultaneously differentiates types 1 and 2. J. Clin. Microbiol. 44, 3443-3447 (2006).*

Zeschnigk, M. et al. A novel real-time PCR assay for quantitative analysis of methylated alleles (QAMA): analysis of the retinoblastoma locus. Nucleic Acids Res. 32, e125 (2004).*
Zou, H. et al. Quantification of methylated markers with a multiplex methylation-specific technology. Clin. Chem. 58, 375-383 (2012).*
Gevertz, J. L., Dunn, S. M. & Roth, C. M. Mathematical model of real-time PCR kinetics. Biotechnology and Bioengineering 92, 346-355 (2005).*
Ballabio, et al., "Screening for steroid sulfatase (STS) gene deletions by multiplex DNA amplification," Human Genetics, 1990, 84(6): 571-573.
Bustin, "Absolute quantification of mRNA using real-time reverse transcription polymerase chain reaction assays," J. Molecular Endocrinology, 2000, 25:169-193.
Chamberlain et al., "Deletion screening of the Duchenne muscular dystrophy locus via multiplex DNA amplification," Nucleic Acids Research, 1988, 16(23):11141-11156.
Don et al., "'Touchdown' PCR to circumvent spurious priming during gene amplification," Nucleic Acids Research, 1991, 19(14):4008.
Frommer et al., "A genomic sequencing protocol that yields a positive display of 5-methylcytosine residues in individual DNA strands," PNAS, 1992, 89(5):1827-1831.
Grigg, "Sequencing 5-methylcytosine residues by the bisulphite method," DNA Seq, 1996, 6(4):189-198.
Grigg & Clark, "Sequencing 5-methylcytosine residues in genomic DNA," Bioessays, 1994, 16(6):431-436.
Guilfoyle et al., "Ligation-mediated PCR amplification of specific fragments from a class-II restriction endonuclease total digest," Nucleic Acids Research, 1997, 25:1854-1858.
Hayden et al., "Multiplex-Ready PCR: A new method for multiplexed SSR and SNP genotyping." BMC Genomics, 2008, 9:80.
Hecker et al., "High and low annealing temperatures increase both specificity and yield in touchdown and stepdown PCR," Biotechniques, 1996, 20(3):478-485.
Herman et al., "Methylation-specific PCR: a novel PCR assay for methylation status of CpG islands," PNAS, 1996, 93(13):9821-9826.
Higuchi et al., "A general method of in vitro preparation and specific mutagenesis of DNA fragments: study of protein and DNA interactions," Nucleic Acids Research, 1988, 16(15):7351-7367.
Higuchi et al.,"Kinetic PCR analysis: real-time monitoring of DNA amplification reactions," Biotechnology, 1993, 11:1026-1030.
Higuchi et al., "Simultaneous amplification and detection of specific DNA sequences," Biotechnology, 1992, 10:413-417.
Jaenisch & Bird, "Epigenetic regulation of gene expression: how the genome integrates intrinsic and environmental signals," Nat Gen Suppl, 2003, 33:245-254.
Kalinina et al., "Nanoliter scale PCR with TaqMan detection," Nucleic Acids Research, 1997, 25:1999-2004.

(Continued)

*Primary Examiner* — Soren Harward
(74) *Attorney, Agent, or Firm* — Casimir Jones, S.C.; Mary Ann Brow (57) ABSTRACT

Provided herein is technology relating to evaluating the state of nucleic acids and particularly, but not exclusively, to methods for measuring variations between DNAs, including differences in methylation and mutation.

6 Claims, 7 Drawing Sheets

(56) References Cited

OTHER PUBLICATIONS

Rebrikov & Trofimov, "Real-Time PCR: A Review of Approaches to Data Analysis," Applied Biochemistry and Microbiology, 2006, 42(5):455-463.
Roux, "Using mismatched primer-template pairs in touchdown PCR," Biotechniques, 1994, 16(5):812-814.
Schouten et al., "Relative quantification of 40 nucleic acid sequences by multiplex ligation-dependent probe amplification," Nucleic Acids Research, 2002, 30(12): e57.
Swift-Scanlan et al., "Two-color quantitative multiplex methylation-specific PCR," BioTechniques, 2006, 40:210-219.
Triglia et al., "A procedure for in vitro amplification of DNA segments that lie outside the boundaries of known sequences," Nucleic Acids Res., 1988, 16:8186.
Vogelstein et al., "Digital PCR," PNAS, 1999, 96: 9236-41.

* cited by examiner

| Log Me Vimentin Strands | Me Vimentin Strands | Cp |
|---|---|---|
| 6.30103 | 2000000 | 8.433504 |
| 6.30103 | 2000000 | 7.726787 |
| 5.30103 | 200000 | 11.56731 |
| 5.30103 | 200000 | 10.88674 |
| 4.30103 | 20000 | 14.93354 |
| 4.30103 | 20000 | 14.24909 |
| 3.30103 | 2000 | 17.98212 |
| 3.30103 | 2000 | 17.61321 |
| 2.30103 | 200 | 21.74918 |
| 2.30103 | 200 | 21.01086 |
| | Intercept | 28.88191792 |
| | Slope | -3.3170389 |

B.

| Log Non-Me Vimentin Strands | Non-Me Vimentin Strands | Cp |
|---|---|---|
| 6.30103 | 2000000 | 9.82613 |
| 6.30103 | 2000000 | 9.009704 |
| 5.30103 | 200000 | 13.01644 |
| 5.30103 | 200000 | 12.13106 |
| 4.30103 | 20000 | 16.28337 |
| 4.30103 | 20000 | 15.35863 |
| 3.30103 | 2000 | 19.36285 |
| 3.30103 | 2000 | 18.80344 |
| 2.30103 | 200 | 23.02654 |
| 2.30103 | 200 | 22.15538 |
| | Intercept | 30.02859534 |
| | Slope | -3.2855481 |

FIG. 2

| Unknown Sample | Cp Methylated (Cpm) | Me strands (Strm) | Cp Non Methyl. (Cpnm) | Non-Me Strands (Strnm) |
|---|---|---|---|---|
| 33 | 22.03882 | 115.6149697 | 17.61622 | 5996.122969 |
| 34 | 23.22674 | 50.68593104 | 19.19584 | 1981.948206 |
| 35 | 21.42217 | 177.3853824 | 18.13082 | 4180.663547 |
| 36 | 21.04554 | 230.3890687 | 18.01573 | 4531.838042 |
| 37 | 24.43424 | 21.92087735 | 17.83763 | 5134.302708 |
| 38 | 20.21809 | 409.1817776 | 17.96504 | 4695.72389 |
| 39 | 28.74618 | 1.09880699 | 18.95945 | 2339.056555 |
| 40 | 21.14027 | 215.7263847 | 18.48667 | 3257.89862 |
| 41 | 22.93094 | 62.23910656 | 18.65087 | 2903.762718 |
| 42 | 23.59618 | 39.22030653 | 20.1352 | 1026.090499 |
| 43 | 18.19743 | 1663.765588 | 17.09218 | 8657.032197 |
| 44 | 21.40803 | 179.1350902 | 18.69088 | 2823.472437 |
| 45 | 21.18819 | 208.6683805 | 17.82764 | 5170.375188 |
| 46 | 22.10989 | 110.0495658 | 18.18279 | 4031.1361 |
| 47 | 21.17871 | 210.0460971 | 17.09821 | 8620.525136 |
| 48 | 21.70964 | 145.295841 | 16.95209 | 9550.085863 |
| 49 | 21.2359 | 201.8707215 | 18.12957 | 4184.327529 |
| 50 | 21.56507 | 160.6339121 | 15.84595 | 20733.64263 |
| 51 | 22.97013 | 60.56874782 | 18.14545 | 4138.018079 |
| 52 | 26.73754 | 4.430712313 | 19.2869 | 1859.417808 |
| 53 | 21.3212 | 190.2644405 | 16.50691 | 13046.79068 |
| 54 | 18.40799 | 1437.519797 | 17.36107 | 7170.159332 |
| 55 | 24.31859 | 23.75326784 | 19.44327 | 1666.417084 |
| 56 | 18.59258 | 1264.633854 | 19.84983 | 1253.261789 |
| 57 | 20.03367 | 465.0654375 | 16.14684 | 16791.74225 |
| 58 | 17.98037 | 1934.327559 | 13.07014 | 145054.1235 |
| 59 | 22.28594 | 97.38989287 | 19.26881 | 1883.141337 |
| 60 | 21.31149 | 191.5512269 | 16.21322 | 16028.47222 |
| 61 | 21.71966 | 144.2887319 | 18.92026 | 2404.189616 |
| 62 | 23.59802 | 39.17024356 | 18.01026 | 4549.244173 |
| 63 | 21.19476 | 207.7188757 | 19.69515 | 1396.756501 |
| 64 | 22.55932 | 80.55583565 | 18.04104 | 4452.161888 |
| 65 | 20.75203 | 282.453796 | 17.7446 | 5480.19965 |
| 66 | 22.78071 | 69.08022511 | 17.63081 | 5935.125018 |
| 67 | 18.6211 | 1239.843226 | 18.17198 | 4061.79151 |
| 68 | 21.85138 | 131.6807527 | 18.07986 | 4332.669554 |

FIG. 2 (continued)

| Unknown Sample | Cp Methylated (Cpm) | Me strands (Strm) | Cp Non Methyl. (Cpnm) | Non-Me Strands (Strnm) |
|---|---|---|---|---|
| 69 | 23.50975 | 41.64543049 | 17.18417 | 8116.534895 |
| 70 | 50 | <1 | 50 | <1 |
| 71 | 18.55116 | 1301.522992 | 15.52774 | 25913.55694 |
| 72 | 22.09694 | 111.0433149 | 17.40737 | 6941.235661 |
| 73 | 22.4511 | 86.8405352 | 18.91976 | 2405.032219 |
| 74 | 17.83021 | 2146.838181 | 15.18222 | 33013.42698 |
| 75 | 22.37267 | 91.69952243 | 18.18603 | 4021.993129 |
| 76 | 24.90457 | 15.81487652 | 20.03347 | 1101.916121 |
| 77 | 21.4055 | 179.4499721 | 17.1715 | 8188.925916 |
| 78 | 20.0616 | 456.1355324 | 16.05258 | 17938.45504 |
| 79 | 18.59345 | 1263.870338 | 16.60206 | 12205.16161 |
| 80 | 23.103 | 55.23212904 | 17.59241 | 6097.017184 |

FIG. 3

| Unknown Sample | Measured % Me 100 x (Strm/Strm+Strnm) | Cp ratio R $10^{(Cpm-Cpnm+Cpof)/-S)}$ | Predicted % Me 100 x (R/(R+1)) |
|---|---|---|---|
| 33 | 1.891687288 | 0.020480159 | 2.006914025 |
| 34 | 2.493608177 | 0.026917226 | 2.62116804 |
| 35 | 4.070293502 | 0.045095828 | 4.314994532 |
| 36 | 4.837842954 | 0.054124128 | 5.134511787 |
| 37 | 0.425134345 | 0.004493062 | 0.447296482 |
| 38 | 8.015462073 | 0.093062074 | 8.513887386 |
| 39 | 0.046954446 | 0.000485109 | 0.048487385 |
| 40 | 6.210410865 | 0.070371035 | 6.574452486 |
| 41 | 2.098417676 | 0.022621648 | 2.212122944 |
| 42 | 3.681583471 | 0.040062065 | 3.85189178 |
| 43 | 16.12051338 | 0.207295994 | 17.17027099 |
| 44 | 5.965984183 | 0.0673188 | 6.307281356 |
| 45 | 3.879284075 | 0.04297013 | 4.119977042 |
| 46 | 2.657441002 | 0.028939089 | 2.81251717 |
| 47 | 2.378624118 | 0.026001596 | 2.534264639 |
| 48 | 1.498608775 | 0.016211878 | 1.595324616 |
| 49 | 4.602407596 | 0.05131012 | 4.880588422 |
| 50 | 0.768793845 | 0.008287976 | 0.821985008 |
| 51 | 1.442598434 | 0.015470021 | 1.523434556 |
| 52 | 0.237718477 | 0.00247597 | 0.246985515 |
| 53 | 1.437362304 | 0.015582581 | 1.534348986 |
| 54 | 16.7004343 | 0.215906972 | 17.75686602 |
| 55 | 1.405377145 | 0.014932945 | 1.471323273 |
| 56 | 50.2258248 | 1.077705254 | 51.86997779 |
| 57 | 2.694967956 | 0.029763766 | 2.890348913 |
| 58 | 1.315972476 | 0.014573594 | 1.436425518 |
| 59 | 4.917362141 | 0.054605116 | 5.177778401 |
| 60 | 1.180955302 | 0.012781589 | 1.262028175 |
| 61 | 5.661760165 | 0.063564132 | 5.976520845 |
| 62 | 0.853677109 | 0.009083528 | 0.900175998 |
| 63 | 12.94621773 | 0.157430139 | 13.60169687 |
| 64 | 1.777208301 | 0.019157525 | 1.879741279 |
| 65 | 4.901453795 | 0.054975948 | 5.211109138 |
| 66 | 1.150530708 | 0.012329328 | 1.217916671 |
| 67 | 23.3860552 | 0.327656043 | 24.67928682 |

FIG. 3 (continued)

| Unknown Sample | Measured % Me 100 x (Strm/Strm+Strnm) | Cp ratio R $10^{(Cpm-Cpnm+Cpof)/-S}$ | Predicted % Me 100 x (R/(R+1)) |
|---|---|---|---|
| 69 | 0.510474503 | 0.005428411 | 0.539910252 |
| 70 | 0 | 0 | 0 |
| 71 | 4.782359615 | 0.054365986 | 5.15627279 |
| 72 | 1.574573486 | 0.01699939 | 1.671524094 |
| 73 | 3.484950629 | 0.038142761 | 3.674134423 |
| 74 | 6.105864593 | 0.070647035 | 6.598536461 |
| 75 | 2.22912916 | 0.024145509 | 2.357624841 |
| 76 | 1.414909004 | 0.01497698 | 1.475597973 |
| 77 | 2.144382309 | 0.023360646 | 2.282738358 |
| 78 | 2.479726474 | 0.02733132 | 2.660419225 |
| 79 | 9.38352766 | 0.111702691 | 10.04789249 |
| 80 | 0.897755052 | 0.009586043 | 0.949502376 |

12
METHODS FOR QUANTIFYING NUCLEIC ACID VARIATIONS

FIELD OF INVENTION

Provided herein is technology relating to evaluating the state of nucleic acids and particularly, but not exclusively, to methods for measuring variations between DNAs, including differences in methylation and mutation.

BACKGROUND

DNA methylation is an epigenetic modification that regulates gene expression and marks imprinted genes. Consequently, aberrant DNA methylation is known to disrupt embryonic development and cell cycle regulation, and it can promote oncogenesis that produces cancers. In mammals, methylation occurs only at cytosine residues and more specifically only on a cytosine residue that is adjacent to a guanosine residue (that is, at the sequence CG, often denoted "CpG"). Detecting and mapping sites of DNA methylation are essential steps for understanding epigenetic gene regulation and providing diagnostic tools for identifying cancers and other disease states associated with errors in gene regulation.

Mapping methylation sites is currently accomplished by the bisulfite method described by Frommer, et al. for the detection of 5-methylcytosines in DNA (*Proc. Natl. Acad. Sci. USA* 89: 1827-31 (1992), explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

A gene's methylation state or mutation/polymorphism state is often expressed as the fraction or percentage of individual strands of DNA that are methylated/mutant at a particular site (e.g., at a single nucleotide or at a longer sequence of interest, e.g., up to a ~100-bp subsequence of a DNA) relative to the total population of DNA in the sample comprising that particular site. For simplicity, the discussion below is directed to measuring methylation but it is equally applicable to the measurement of mutations and polymorphism in nucleic acid populations.

Traditionally, the amount of unmethylated (e.g., native) gene is determined by quantitative PCR (qPCR) using calibrators. Then, a known amount of DNA is bisulfite treated and the resulting methylation-specific sequence is determined using either a real-time PCR or an equivalent exponential amplification. In particular, conventional methods generally comprise generating a standard curve for the unmethylated target by using external standards. The standard curve is constructed from at least two points and relates the real-time $C_p$ value for unmethylated DNA to known quantitative standards. Then, a second standard curve for the methylated target is constructed from at least two points and external standards. This second standard curve relates the $C_p$ for methylated DNA to known quantitative standards. Next, the test sample $C_p$ values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Accordingly, these conventional methods require the construction of standard curves from several external standard PCRs and then require calculating a putative absolute number of methylated DNA sites or strands in one portion of the test sample and a putative absolute number of unmethylated sites or strands of DNA from another portion of the test sample. These methods require the user to assemble several reaction mixtures, which can be labor intensive and time-inefficient, and which increases the likelihood of error. In addition, the number of reactions requires a relatively large amount of DNA to provide enough template for all the necessary PCR mixtures, and thus is sample-inefficient. Furthermore, each of the numerous measurements has an associated error that is propagated in calculating the extent of methylation in the test sample. In particular, at least two standards are assembled and measured to construct the methylated DNA standard curve, at least two standards are assembled and measured to construct the unmethylated DNA standard curve, and multiple aliquots of the test sample are assembled and measured. Additionally, well-to-well variation (e.g., amongst the wells of a 96-well assay plate) between external standards and the test sample can also introduce significant errors in the measurement. For instance, the typical calibration methods used for fluorescence real-time PCR thermocyclers can unpredictably produce well-to-well variations of 1 $C_p$ unit or more. As such, these variations in sample measurement as a function of location on the assay plate can cause substantial errors for the analysis of a test sample.

SUMMARY

The present technology provides methods and systems for determining the fractional amount of a nucleic acid target that is variant, e.g., as compared to a reference or non-variant nucleic acid, expressed as percent variant of said nucleic acid target. The nature of the variation is not limited to any particular type of variation. For example, in some embodiments, the variation may be a particular methylation status, e.g, the percentage of a nucleic acid that is methylated compared to the amount of the same target nucleic acid that is not methylated. In some embodiments, the technology relates to determining the percentage of target nucleic acid that contains a mutation or polymorphism or particular allele, compared to the target nucleic acid that does not contain the particular mutation or polymorphism or allele of interest.

In some embodiments, methods of the technology comprise the steps of:

a) providing quantitative amplification data from a sample comprising nucleic acid target, wherein said nucleic acid target comprises at least one copy of a non-variant form of said nucleic acid target and/or at least one copy of a variant form of said nucleic acid target, wherein said quantitative amplification data correlates to amplification cycle numbers for said non-variant and variant forms of said nucleic acid target present in said sample;

b) determining a first crossing threshold indicative of variant copies of said nucleic acid target ($C_pv$);

c) determining a second crossing threshold indicative of non-variant copies of said nucleic acid target ($C_pnv$); and d) calculating a ratio R of variant copies of said nucleic acid target to non-variant copies of said nucleic acid target, and e) calculating the percentage of nucleic acid target present in said sample that is variant form.

In some embodiments, prior to calculating of the ratio R, the method comprises a step of determining a log copy number for the variant and non-variant copies of the target nucleic acid. In certain preferred embodiments, the log copy number for variant copies of said target nucleic acid is described by "log copy=$(C_pv-C_p0)/-S$" and the log copy number for non-variant copies of the target nucleic acid is described by "log copy=$(C_pnv-C_p0)/-S$," wherein $C_p0$ is the intercept of the y axis when log copy number=0 and wherein S=the slope of the linear regression of reaction efficiency. In some embodiments, the method further comprises calculating an offset $C_p$off between the regression lines of $C_pv$ and $C_pnv$.

In certain preferred embodiments, the ratio R is calculated according to the expression "ratio R=$10^{(Cpv-Cpnv+Cpoff)/-S)}$." In still further preferred embodiments, the percentage of nucleic acid target in the sample that is variant form is calculated as according to the expression "percent variant=$100 \times (R/(R+1))$."

In some embodiments, the value for S is a value estimated from a range for use in the calculation of the log copy values. In some embodiments, the value used for S is greater than or equal to about 2.7, while in some embodiments, the value used for S is less than or equal to about 3.3. In certain preferred embodiments, the value used for S is 3.

The quantitative amplification data is not limited to data from any particular type of reaction. It is contemplated that the technology finds use in, for example, ligase chain reactions, transcription mediated amplification, scorpion probe-based assays, etc. In some embodiments, the quantitative amplification data is from a quantitative PCR assay (including, e.g., reverse-transcription PCR detection of RNA), such as a real time quantitative polymerase chain reaction. In certain preferred embodiments, the quantitative PCR assay is a PCR+INVADER assay. In particularly preferred embodiments, the PCR+INVADER assay is a QuARTS assay.

It is contemplated that the data is collected from any detectable signal or attribute of amplification products, e.g., fluorescence, luminescence, radiation, polarization, mass, etc. In certain preferred embodiments, the quantitative amplification data comprises fluorescence data.

The technology of the invention finds application for the analysis of any type of variation between two or more nucleic acids in a sample. For example, in some embodiments, the variation relates to methylation, e.g., variant nucleic acid is methylated DNA and said non-variant nucleic acid is unmethylated DNA, or vice versa. In other embodiments, the variant nucleic acid is nucleic acid containing a mutation, polymorphism, or other sequence-based difference, and the non-variant nucleic acid is wild type nucleic acid, or any nucleic acid to which the variant is to be compared such that the relative fractions represented by the variants and non-variants constitute 100% of the copies of interest. For example, the technology also finds use in detecting relative amounts of two or more mutations in a sample.

The technology may also be applied using a reference gene that is unrelated to the target nucleic acid, e.g., a gene that is present in the sample in copy numbers that are the same as the copy numbers of the target of being measured. For example, the portion of a single copy gene that is methylated in a sample may be quantified by comparison to another single copy gene. Thus, in some embodiments, the technology provides method to determine the fractional amount of a nucleic acid target that is variant, comprising the steps of:

a) providing a sample comprising:
   i) a population of copies of the nucleic acid target, wherein the population of copies of the nucleic acid target comprises at least one non-variant copy of the nucleic acid target, and/or at least one variant copy of the nucleic acid target, and
   ii) a population of copies of a reference nucleic acid target, wherein said population of copies of the reference nucleic acid target in said sample contains approximately the same number of copies as said population of copies of the nucleic acid target;

b) treating the test sample with a quantitative amplification assay to produce quantitative amplification data from the sample, wherein the quantitative amplification data correlates to amplification cycle number for said variant form of said nucleic acid target and said reference nucleic acid target;

c) determining a first crossing threshold indicative of copies of said variant form of said nucleic acid target ($C_pv$);

d) determining a second crossing threshold indicative of copies of said reference nucleic acid target ($C_pr$); and e) calculating a ratio R of copies of said variant form of said nucleic acid target to copies of said reference target nucleic acid, and f) calculating the percent variant of said target nucleic acid present in said sample.

As with the method discussed above, in some embodiments, prior to calculating the ratio R, said method comprises a step of determining a log copy number for copies of the variant nucleic acid target and for copies of the reference nucleic acid target. In certain preferred embodiments, the log copy number for copies of the variant form of the nucleic acid target is described by the expression "log copy=$(C_pv-C_p0)/-S$," and the log copy number for the reference nucleic acid target is described by "log copy=$(C_pr-C_p0)/-S$," wherein $C_p0$ is the intercept of the y axis when log copy number=0, and wherein S=the slope of the linear regression of reaction efficiency. In some embodiments, the method further comprises calculating an offset $C_p$off between the regression lines of $C_pv$ and $C_pr$.

In some embodiments, the ratio R is calculated according to the expression ratio R=$10^{(Cpv-Cpr+Cpoff)/-S)}$. In certain preferred embodiments, the percentage of the nucleic acid target that is variant form is calculated according to the expression "percent variant=$100 \times R$."

In some embodiments, the reference nucleic acid target comprises a nucleic acid encoding at least a portion of a housekeeping protein, and in certain preferred embodiments, the housekeeping protein is an actin polypeptide, e.g., α-actin. As discussed above, the technology of the invention is not limited to any particular variation in its application. Variations of nucleic acid targets include methylation, mutation, deletion, polymorphism, alleleic differences, etc.

BRIEF DESCRIPTION OF THE DRAWINGS

These and other features, aspects, and advantages of the present technology will become better understood with regard to the following drawings:

FIG. 1A shows the measured Cps for methylated vimentin strands. FIG. 1B shows the measured Cps for non-methylated vimentin strands.

DETAILED DESCRIPTION

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

The term "target," when used in reference to a nucleic acid capture, detection, or analysis method, generally refers to a nucleic acid having a feature, e.g., a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or basepair. As used herein in reference to CpG sites that may be methylated, a locus refers to the C residue in the CpG dinucleotide.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et alet al. (1988) Nucleic Acids Res., 16:8186; herein incorporated by reference in its entirety), ligation-mediated PCR (see, e.g., Guilfoyle, R. et alet al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes.

Additional amplification plus invasive cleavage detection configurations, termed the QuARTS method, are described in U.S. patent application Ser. No. 12/946,737 (now U.S. Pat. No. 8,361,720); Ser. No. 12/946,745 (now U.S. Pat. No. 8,916,344); and Ser. No. 12/946,752 (now U.S. Pat. No. 8,361,720), incorporated herein by reference in their entireties for all purposes. In performing the QuARTS method, the reaction mixture is generally subjected to the following thermocycling conditions:

1. a first set of 5 to 15 (e.g., 8 to 12) cycles of:
  i) a first temperature of at least 90° C.;
  ii) a second temperature in the range of 60° C. to 75° C. (e.g., 65° C. to 75° C.);
  iii) a third temperature in the range of 65° C. to 75° C.; followed by:
  a second set of 20-50 cycles of:
  i) a fourth temperature of at least 90° C.;
  ii) a fifth temperature that is at least 10° C. lower than the second temperature (e.g., in the range of 50° C. to 55° C.; and
  iii) a sixth temperature in the range of 65° C. to 75° C.

No additional reagents need to be added to the reaction mixture during the thermocycling, e.g., between the first and second sets of cycles. In particular embodiments, the thermostable polymerase is not inactivated between the first and second sets of conditions, thereby allowing the target to be amplified during each cycle of the second set of cycles. In particular embodiments, the second and third temperatures are the same temperature such that "two step" thermocycling conditions are performed. Each of the cycles may be independently of a duration in the range of 10 seconds to 3 minutes, although durations outside of this range are readily employed.

In each cycle of the second set of cycles (e.g., while the reaction is in the fifth temperature), a signal generated by cleavage of the flap probe may be measured to provide a real-time measurement of the amount of target nucleic acid in the sample (where the term "real-time" is intended to refer to a measurement that is taken as the reaction progresses and products accumulate). The measurement may be expressed as an absolute number of copies or a relative amount when normalized to a control nucleic acid in the sample.

Without being bound to any specific theory, it is believed that the higher reaction temperatures in the first set of cycles may allow the target nucleic acid to be efficiently amplified by the pair of PCR primers without significant interference by any of the flap assay reagents or their reaction products. The lower reaction temperature used in the second set of cycles (i.e., the fifth temperature) is not optimum for the polymerase used for PCR, but allows the flap oligonucleotide to efficiently hybridize to the target nucleic acid and is closer to the optimum temperature of the flap endonuclease. The lower reaction temperature used in the second set of cycles also facilitates subsequent hybridization of the cleaved flap to the FRET cassette. Thus, at a lower temperature, the target nucleic acid may be detected without significant interference from the PCR reagents.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "gene" refers to a nucleic acid (e.g., DNA) sequence that comprises coding sequences necessary for the production of a polypeptide, precursor, or RNA (e.g., rRNA, tRNA). A polypeptide can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The abbreviations "Ct" and "Cp" as used herein in reference to data collected during real time PCR and PCR+INVADER assays refer to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

As used herein, the term "kit" refers to any delivery system for delivering materials. In the context of nucleic acid purification systems and reaction assays, such delivery systems include systems that allow for the storage, transport, or delivery of reagents and devices (e.g., inhibitor adsorbents, particles, denaturants, oligonucleotides, spin filters etc. in the appropriate containers) and/or supporting materials (e.g., buffers, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an materials for sample collection and a buffer, while a second container contains capture oligonucleotides and a denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

DETAILED DESCRIPTION OF THE INVENTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. For example, while the invention is discussed in terms of measuring methylation of DNA, it is to be understood that the methods and systems discussed in this Description and in the Summary of the Invention also encompass methods for measuring a percentage of mutation or polymorphism in a nucleic acid target.

Provided herein is a multiplexed, quantitative assay for determining a percent methylation or other variation (e.g., mutation, polymorphism, deletion) of a target nucleic acid without reference to external standards, curves or controls. In certain embodiments, the assay comprises a combined amplification reaction (e.g., polymerase chain reaction) with a signal-generating system (e.g., INVADER assay invasive cleavage reaction). In certain embodiments, a mixture of target nucleic acids, e.g., bisulfite-treated non-methylated and methylated DNAs, are treated using PCR+INVADER assays configured to quantitatively emit signal from different labels. For example, in some embodiments, bisulfite-treated non-methylated DNA is detected using a first dye (e.g., FAM dye), and bisulfite-treated methylated DNA is detected using a second dye (e.g., CAL RED dye), with both assays conducted in the same vessel, at the same time. Although the two assays amplify simultaneously and in the same reaction well or vessel, they are detected in different channels. The concentration of nucleic acid target going into the reaction may vary, as may the percent methylation or variation. In some embodiments, percent methylation of a target nucleic acid correlates with clinical presence of cancer, advanced adenoma. Normal samples have low to absent methylation and adenoma and cancers can be greater than 90% methylated.

As noted above, real time thermal cycling detection reactions, such as real time qPCR monitor signal as a function of the number of thermal cycles. Typically, one measure of the amount of target nucleic acid in a sample is the cycle at which signal (e.g., fluorescent signal) crosses a predetermined threshold value indicative of signal that is above background noise. Various methods have been used to calculate the threshold that is used as a determinant of signal that is above background and is thus indicative of target concentration, and the value is generally expressed as either the crossing threshold (Ct) or the crossing point (Cp). The particular signal level set as the threshold is influenced by the particular chemistry of a reaction and the instrumentation used to measure the real-time signal, and is generally set just above the baseline signal (noise) measured in early cycles, before significant target or signal amplification has occurred. In some embodiments, a Ct or Cp is set as a percentage of the maximum signal, e.g., a percentage of the highest level of fluorescence measured in a calibrator or control measured during the same experiment (e.g., in a well on the same plate in a thermalcycling instrument).

Because the signal and crossing point vary from assay to assay, when using prior methods, a standard curve is typically run at the same time, and unknown samples are interpolated from the curve. The standard curve is typically from a dilution series of target nucleic acid at known concentrations. While the precision of the Cps run in the same assay (e.g., in different wells, but on the same reaction plate) can be very high, real time PCR can be imprecise (>25% CV) run-to-run, even with a standard curve.

In embodiments of the present invention, the ratio of different species of DNA in a sample (e.g., methylated to non-methylated; mutant to wild type; etc.) is determined without reference to external standards or controls (i.e., without reference to controls that are not within the same reaction tube, well or other vessel containing the reaction mixture).

In the following discussion, the crossing point indicative of real signal is referred to as "Cp" but the discussion is equally applicable to analysis of threshold cycles ("Ct") and other measures of the cycle at which a positive signal is detected in a real-time detection assay.

Since the relationship of Cp to concentration is a linear log relationship and there is roughly a doubling of target at each cycle, the log copy number (or concentration) is described by $$\text{Log copy} = (C_p x - C_p 0)/-3.3$$

where $C_p x$ is the crossing point of the unknown and $C_p 0$ is the intercept of the y axis where log copy number=0. 3.3 is the slope of the linear regression for a PCR having 100% efficiency (i.e., perfect doubling).

Typically, however, the measured slope varies based on the actual doubling efficiency of the assay. Further, for the PCR+INVADER assay, the PCR amplification is coupled to signal amplification from the INVADER invasive cleavage assay. The slope for PCR+INVADER assays, such as the QuARTS assay, the slope can be less than 2.7. If the slope in the range of about 2.7 to 3.3, then using 3 as a value for slope value will be acceptable and will have little effect on the result.

For multiplexed PCR and PCR+INVADER assays (e.g., detection of two or more different targets, alleles, etc.) the assays are performed together and they can have the same slope and intercept, or they can have known differences in slope and intercept. In certain preferred embodiments, the two assays are configured to have the same slope and intercept.

In determining the relative proportions of variants in a mixture, the sum of the signals (e.g., the signal from methylated DNA, plus the signal from unmethylated DNA of a gene or locus) necessarily represents the total (100%) of the target DNA in the test sample. One can therefore calculate the percent methylation by comparing the two signals to each other, without the need to determine an absolute concentration of the target nucleic acids. The ratio of signals can be determined by the following calculation $$\text{Ratio} = 10^{((C_p m - C_p nm + C_p \text{off})/-S)}$$

where $C_p m$ is the crossing threshold/crossing point for the methylated target, $C_p nm$ is the crossing point for the non-methylated target and $C_p \text{off}$ is the offset Cp between the two regression lines of $C_p nm$ or $C_p m$ vs. the log concentration of non-methylated or methylated target, respectively. If the lines are superimposable, then $C_p \text{off}$ is 0. S is the slope of the linear regression for $C_p$ vs log copy number for both targets. As noted above, for a slope in the range 2.7 to 3.3, using 3 will be acceptable and have little effect on the result.

The same equation can be used for analysis of any variation in a nucleic acid population, e.g., mutation, polymorphism, allele copy number, etc. The general version of the equation may be presented as follows:

$$\text{Ratio}(R) = 10^{((C_p v - C_p nv + C_p \text{off})/-S)}$$

where "v" and "nv" represent variant and nonvariant components of the sample.

Once the ratio has been calculated, then the fraction of, or percent methylation can be calculated as follows $$\% \text{ methylation} = 100 \times (R/(R+1))$$

where R is the Ratio. The absolute copy number is not required to calculate the percent methylation.

In some embodiments, a reference gene, e.g., a gene known to be present in an invariant number of copies per genome, such as actin, is used. If a reference gene is used and both the reference gene and the methylated gene are single copy genes, it is possible to use only the ratio equation to arrive at % methylation:

$$R*100 = \% \text{ methylation}$$

Figure 1:
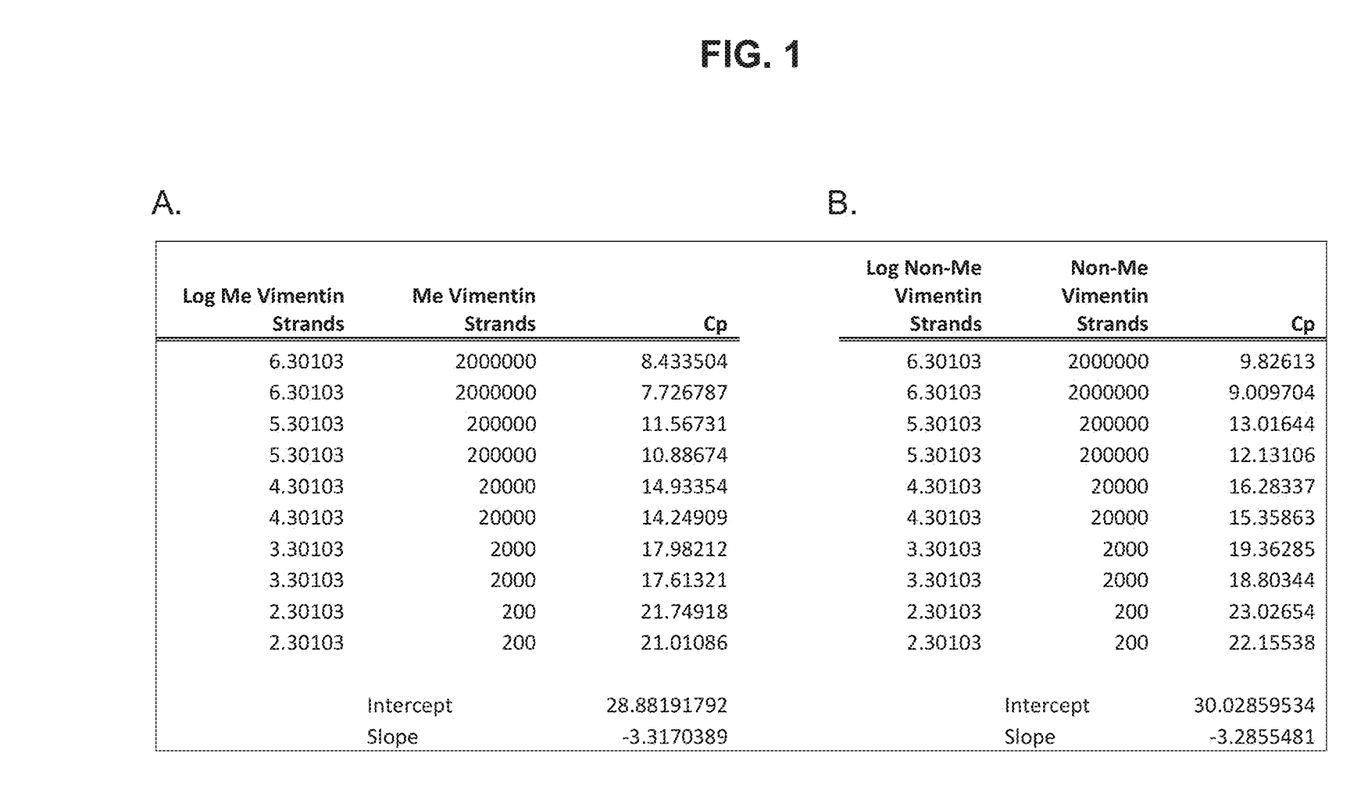
FIG. 1 shows threshold crossing point (Cp) as measured using a series of control samples having the indicated number of strands of vimentin target nucleic acid. Methylated and non-methylated target strands were measured together in the same assay and in the same reaction vessel. One copy of double-stranded DNA is counted as two strands.
Figure 2:
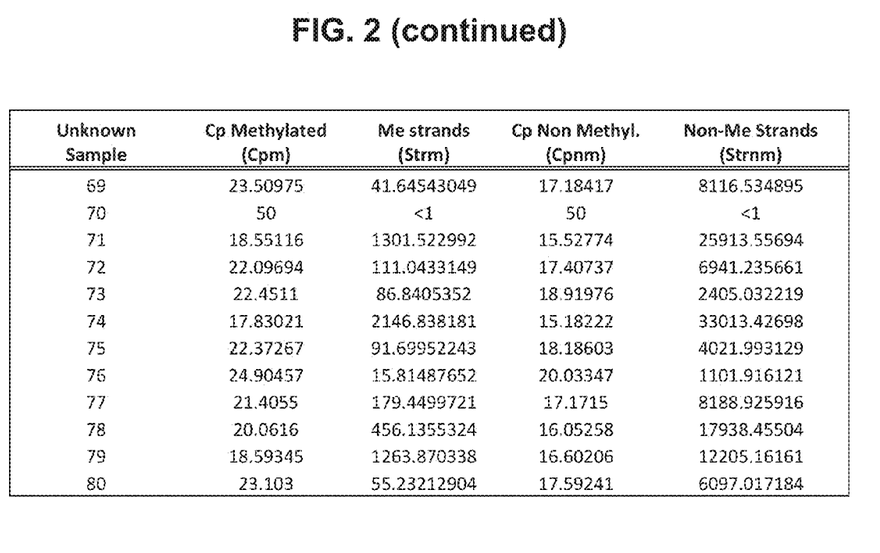
FIG. 2 shows the measured Cps for methylated (Me) and non-methylated (Non Me) vimentin DNA from samples numbered 33-80. The numbers of Me and Non-Me strands are calculated by reference to the standards shown in FIG. 1.
Figure 3:
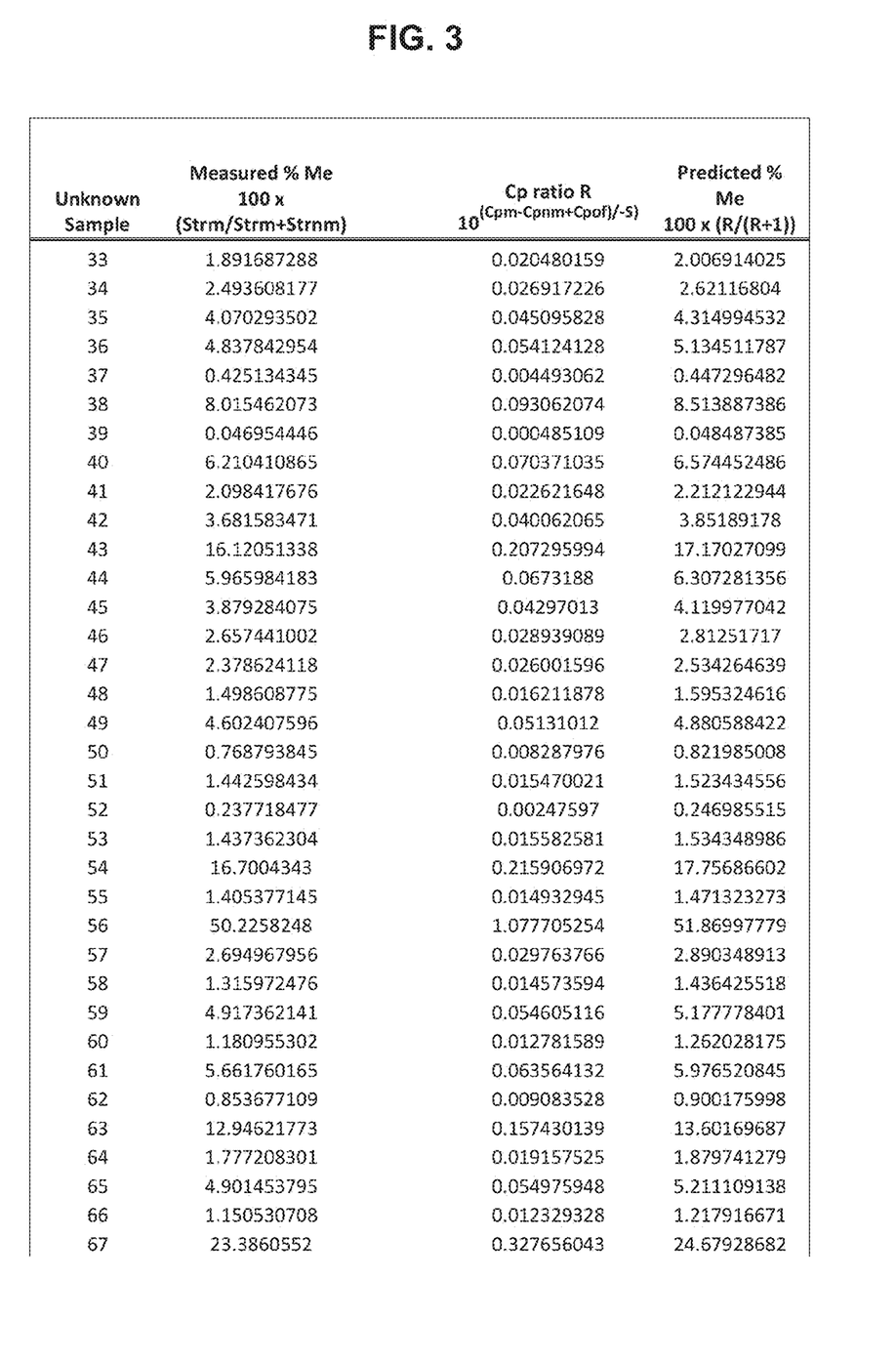
FIG. 3 shows the percentage of methylated vimentin DNA calculated from the strand counts in FIG. 2 for each of samples 33-80, compared to the percentage of methylation in the same set of samples predicted by comparing the Cp values for each sample using the methods of the invention. The formulae for calculating the percentage methylation from the values measured for methylated strands (Strm) and non-methylated strands (Strnm) in FIG. 2, and for calculating a Cp ratio R and predicting a % methylation value from R for each sample are shown in the header of the table.
Figure 4:
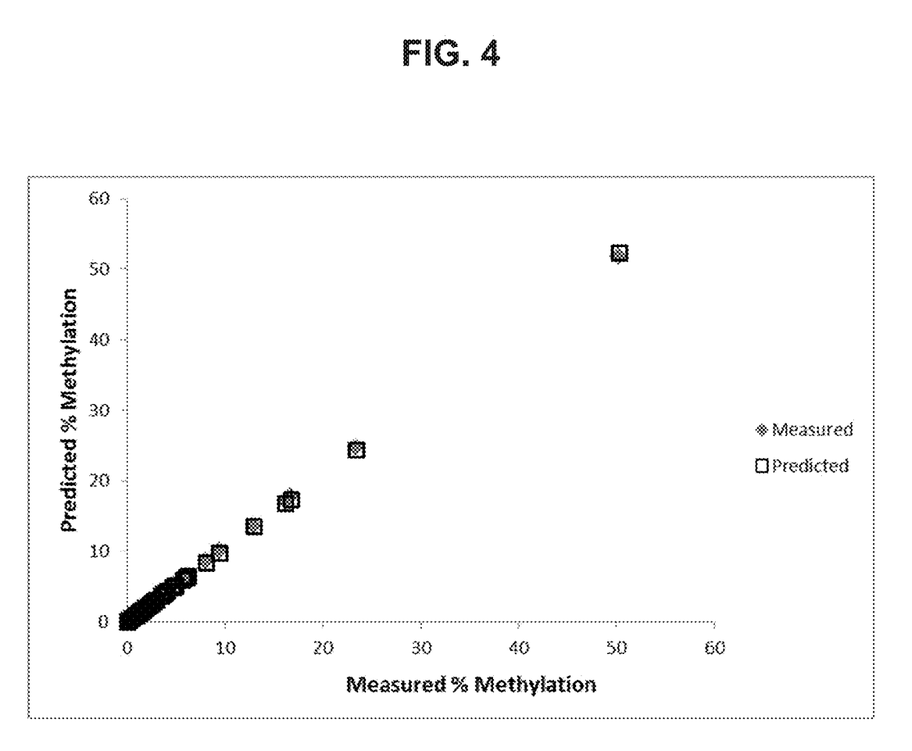
FIG. 4 shows a graph comparing the percent methylation calculated for each sample by comparison to external standards ("measured" % methylation) to the percent methylation predicted for each sample by analysis of Cpm and Cpnm values measured for the same sample (predicted % methylation).
Figure 5:
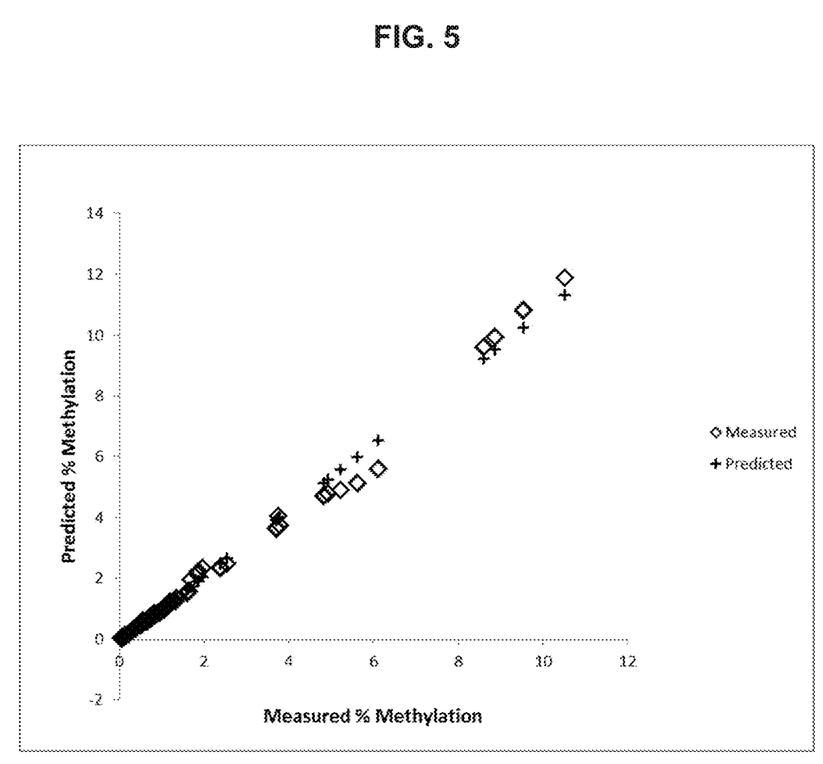
FIG. 5 shows a graph comparing the percent methylation calculated for vimentin DNAs in each sample by comparison to external vimentin standards ("calculated % methylation") to the percent methylation predicted by analysis of Cp values measured for actin and methylated vimentin the same sample ("predicted % methylation").

Exemplary data comparing the percent methylation calculated for a vimentin gene compared to the percent methylation predicted using the methods described above In this embodiment, the reference gene is present in the same number of copies as the sum of the methylated and non-methylated copies of the test gene.

The methods can also be used to calculate percent mutation (or polymorphism) in a target gene. For example, KRAS mutations can be used to identify colon cancer and adenoma. By determining the ratio of the copies containing mutation to either the wild type sequence or to a reference gene having the same copy number, an estimate of % mutation can be obtained and used to differentiate normal DNA samples from cancer DNA samples.

Although the disclosure herein refers to certain illustrated embodiments, it is to be understood that these embodiments are presented by way of example and not by way of limitation.

EXAMPLES

Measurement of Methylated and Unmethylated Vimentin Gene Sequences

Embodiments of the present invention are used to quantitate the methylated CpG sequences of vimentin (VIM) in the presence of unmethylated VIM sequence. In order to simulate the methylated and unmethylated genomic DNA, plasmids may be prepared and cloned to match the sequence that results following the bisulfate reaction conversion of unmethylated C to U, which behaves as if it were a T in the PCR process. The methylated version of the sequence uses a plasmid with the CpG motif intact and the unmethylated representative plasmid replaces this with a TpG motif.

In this example, 3 CpGs are designed on each primer of the vimentin methylation detection assay, with one at the 3' end of the forward primer. In this assay, the forward primer is also the invasive oligonucleotide. There are also CpG motifs located at the cleavage point of the flap probe, in both senses. The assay is then used to detect methylated copies spiked in unmethylated copies at different levels.

A target sequence of the plasmid representing the methylated sequence is as follows, with every C base corresponding to a methyl C for an analogous genomic DNA:

(SEQ ID NO.: 1)
5'TCGTGTTTTCGTTTTTTTATCGTAGGATGTTCGGCGGTTCGGGTAT

CGCGAGTCGGTCGAGTTTTAGTCGGAGTTACGTGATTACGTTTATTCG

TATTTATAGTTTGGGCGACG 3'

An exemplary assay employs a forward primer 5'-GGCGGTTCGGGTATCG-3' (SEQ ID NO.:2), a reverse primer 5'-CGTAATCACGTAACTCCGACT-3' (SEQ ID NO.:3), and a flap probe 5'-GACGCGGAGGCGAGTCGGTCG-3'/3C6 (SEQ ID NO.:4) where the area corresponding to methylated bases is shown underlined and the 3'-end is blocked, e.g., with a hexanediol or amino group in order to inhibit primer extension. The first nine bases of the flap probe in this example are the region cleaved away by the flap endonuclease, and that then bind to a FRET cassette. Primers and flap probes are generally supplied as non-catalog items by Integrated DNA Technologies (IDT, Coralville, Iowa).

A FRET cassette usable with these primer and probe oligonucleotides is 5'-FAM/TCT/Quencher/AGCCGGTTTTCCGGCT GAGACTCCGCGTCCGT-3'/3C6 (SEQ ID NO.:5), where FAM is fluorescein, the quencher is the ECLIPSE Dark Quencher, and the 3'-end is blocked, e.g., with a hexanediol group.

Exemplary cycling conditions are 95° C. for 2 min; 45 cycles at 95° C. for 20 sec, 53° C. for 1 min; and 40° C. to hold. Fluorescent signal acquisition is done, e.g., at the 53° C. point in the cycle. The PCR reactions may be done, e.g., in LightCycler 480 Multiwell 96 Plates (Roche, Indianapolis) in 10 mM MOPS pH 7.5, with 7.5 mM $MgCl_2$, and 250 µM dNTPs (Promega, Madison, Wis.). In some embodiments, Taq polymerase is the HotStart GoTaq enzyme (Promega, Madison, Wis.) and the cleavage enzyme was Cleavase 2.0 (Hologic, Inc., Madison, Wis.). In some embodiments. forward primer concentration is 500 nM, reverse primer concentration is 500 nM, flap probe is at 500 nM, and the FRET cassette is used at a final concentration of 200 nM. Amplification and detection may be performed, e.g., in the LightCycler 480 optical thermocycler (Roche, Indianapolis, Ind.). The Cp is calculated as being the point at which fluorescence rises to 18% of the maximum fluorescence.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

I claim:

1. A method of analyzing a sample comprising a nucleic acid target, the method comprising:
   a) providing a sample comprising nucleic acid target, wherein said nucleic acid target comprises at least one copy of a non-variant form of said nucleic acid target and/or at least one copy of a variant form of said nucleic acid target,
   b) providing reagents for an amplification reaction comprising a polymerase chain reaction and an invasive cleavage detection assay, wherein said reagents comprise concentrations of oligonucleotides comprising forward primers and reverse primers complementary to portions of said variant and non-variant forms of said nucleic acid target, FRET cassettes, and flap probes, said flap probes comprising a portion complementary to a region of a nucleic acid target and a flap portion complementary to a region of a FRET cassette,
   wherein the concentrations of said oligonucleotides in said reagents produce quantitative amplification data in said amplification reaction from said variant form and said non-variant form of nucleic acid target, said data having the same known slope S for each form, wherein S=the slope of the linear regression of reaction efficiency; and having previously determined $C_p0$ and $C_p$off values, wherein $C_p0$ is the intercept of the y axis when log copy number=0 and $C_p$off is an offset between regression lines of crossing thresholds of quantitative amplification data from standard curves for said variant and non-variant forms of nucleic acid target;
   wherein in said amplification reaction, non-variant and/or variant nucleic acid target is amplified, and wherein amplified nucleic acid is detected by invasive cleavage to produce quantitative amplification data from said non-variant form and said variant form of said nucleic acid target, and wherein said quantitative amplification data correlates to amplification cycle numbers for said non-variant and variant forms of said nucleic acid target present in said sample;
   c) amplifying said nucleic acid target using the reagents of step b) to produce quantitative amplification data from said non-variant form and said variant form of said nucleic acid target, wherein said amplifying comprises subjecting a mixture of said nucleic acid target and the reagents of step b) to the following thermal cycling conditions:
   a first set of 5-15 cycles of:
      i) a first temperature of at least 90° C.;
      ii) a second temperature in the range of 60° C. to 75° C.;
      iii) a third temperature in the range of 65° C. to 75° C.;
   followed by:
   a second set of 20-50 cycles of:
      i) a fourth temperature of at least 90° C.;
      ii) a fifth temperature that is at least 10° C. lower than said second temperature;
      iii) a sixth temperature in the range of 65° C. to 75° C.;
      wherein no additional reagents are added to said reaction between said first and second sets of cycles and, in each cycle of said second set of cycles, cleavage of a flap probe is measured;
   d) determining a first crossing threshold indicative of variant copies of said nucleic acid target ($C_p$v);
   e) determining a second crossing threshold indicative of non-variant copies of said nucleic acid target ($C_p$nv);
   f) calculating a ratio $R=10^{(Cpv-Cpnv+Cpoff)/-S)}$, and
   g) calculating the percentage of nucleic acid target present in said sample that is variant form, wherein the percentage of nucleic acid target in said sample that is variant form is calculated as percent variant=100×(R/(R+1)).

2. The method of claim 1, wherein the value used for S is greater than or equal to about 2.7.

3. The method of claim 1, wherein the value used for S is less than or equal to about 3.3.

4. The method of claim 1, wherein the value used for S is 3.

5. The method of claim 1, wherein said variant nucleic acid is methylated DNA and said non-variant nucleic acid is unmethylated DNA.

6. The method of claim 1, wherein said variant nucleic acid is nucleic acid containing a mutation and said non-variant nucleic acid is wild type nucleic acid.

* * * * *

SEQUENCE LISTING

```
<160> NUMBER OF SEQ ID NOS: 5

<210> SEQ ID NO 1
<211> LENGTH: 114
<212> TYPE: DNA
<213> ORGANISM: Artificial sequence
<220> FEATURE:
<223> OTHER INFORMATION: Synthetic

<400> SEQUENCE: 1
tcgtgttttc gttttttat cgtaggatgt tcggcggttc gggtatcgcg agtcggtcga      60
gttttagtcg gagttacgtg attacgttta ttcgtattta tagtttgggc gacg         114

<210> SEQ ID NO 2
<211> LENGTH: 16
<212> TYPE: DNA
<213> ORGANISM: Artificial sequence
<220> FEATURE:
<223> OTHER INFORMATION: Synthetic

<400> SEQUENCE: 2
ggcggttcgg gtatcg                                                     16

<210> SEQ ID NO 3
<211> LENGTH: 21
<212> TYPE: DNA
<213> ORGANISM: Artificial sequence
<220> FEATURE:
<223> OTHER INFORMATION: Synthetic

<400> SEQUENCE: 3
```

```
cgtaatcacg taactccgac t                                              21

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
gacgcggagg cgagtcggtc g                                              21

<210> SEQ ID NO 5
<211> LENGTH: 32
<212> TYPE: DNA
<213> ORGANISM: Artificial sequence
<220> FEATURE:
<223> OTHER INFORMATION: Synthetic

<400> SEQUENCE: 5
agccggtttt ccggctgaga ctccgcgtcc gt                                  32
```